United States Patent
Feulner et al.

(10) Patent No.: US 9,582,953 B2
(45) Date of Patent: Feb. 28, 2017

(54) METHOD FOR CHECKING A VALUE DOCUMENT

(71) Applicant: GIESECKE & DEVRIENT GMBH, München (DE)

(72) Inventors: Johannes Feulner, München (DE); Jan Domke, Vaterstetten (DE); Norbert Holl, Germering (DE)

(73) Assignee: GIESECKE & DEVRIENT GMBH, Munich (DE)

( * ) Notice: Subject to any disclaimer, the term of this patent is extended or adjusted under 35 U.S.C. 154(b) by 0 days.

(21) Appl. No.: 15/021,548

(22) PCT Filed: Sep. 11, 2014

(86) PCT No.: PCT/EP2014/002466
§ 371 (c)(1),
(2) Date: Mar. 11, 2016

(87) PCT Pub. No.: WO2015/036121
PCT Pub. Date: Mar. 19, 2015

(65) Prior Publication Data
US 2016/0232730 A1     Aug. 11, 2016

(30) Foreign Application Priority Data
Sep. 13, 2013  (DE) ................ 10 2013 015 200

(51) Int. Cl.
*G07F 7/04* (2006.01)
*G07D 7/08* (2006.01)
(Continued)

(52) U.S. Cl.
CPC .............. *G07D 7/08* (2013.01); *G01N 21/33* (2013.01); *G01N 21/35* (2013.01); *G01N 21/59* (2013.01);
(Continued)

(58) Field of Classification Search
CPC .............. G07D 5/00; G07D 7/00; G07D 7/08; G07D 7/12; G07D 11/0033; G07D 11/0051; G07D 11/0069; G07D 11/0078; G07D 11/0084; G07D 11/0087; G07D 2207/00; G07D 2211/00; G07F 3/00; G07F 3/02; G07F 7/00; G07F 7/04; G07F 19/00; G07F 19/20; G07F 19/206; G07F 19/208; G07F 19/211
(Continued)

(56) References Cited

U.S. PATENT DOCUMENTS

| | | |
|---|---|---|
| 5,809,160 A | 9/1998 | Powell et al. |
| 7,873,518 B2 | 1/2011 | Hentschel et al. |

(Continued)

FOREIGN PATENT DOCUMENTS

| | | |
|---|---|---|
| DE | 102004023824 A1 | 12/2005 |
| DE | 102006033001 A1 | 1/2008 |

(Continued)

OTHER PUBLICATIONS

German Search Report from corresponding German Application No. DE 10 2013 015 200.3, Mar. 24, 2014.
(Continued)

*Primary Examiner* — Jeffrey Shapiro
(74) *Attorney, Agent, or Firm* — Workman Nydegger

(57) ABSTRACT

A method is described for checking a value document, wherein measuring values of the value document are detected in spatially resolved fashion. The measuring value detected in the respective measuring point is allocated to a node corresponding to this measuring point, and a two-dimensional network of nodes is formed therefrom. A network is formed from the two-dimensional network of the nodes and a source node and a sink node. By means of the maximally possible flow through the network, the value
(Continued)

document is classified as suspected of forgery or not suspected of forgery. The maximally possible flow through the network is a measure for the degree of probability of the value document having a continuous object along a direction transverse to the direction of the network, said object indicating a manipulation of the value document, such as e.g. an adhesive strip or a separating line of a composed forgery.

16 Claims, 3 Drawing Sheets

(51) Int. Cl.

| | | |
|---|---|---|
| *G07D 7/00* | (2016.01) | |
| *G07D 11/00* | (2006.01) | |
| *G07F 7/00* | (2006.01) | |
| *G07F 19/00* | (2006.01) | |
| *G07D 7/06* | (2006.01) | |
| *G07D 7/18* | (2006.01) | |
| *G07D 7/20* | (2016.01) | |
| *G01N 21/33* | (2006.01) | |
| *G01N 21/35* | (2014.01) | |
| *G01N 21/59* | (2006.01) | |
| *G01N 29/04* | (2006.01) | |
| *G07D 7/12* | (2016.01) | |

(52) U.S. Cl.
CPC .............. *G01N 29/04* (2013.01); *G07D 7/00* (2013.01); *G07D 7/06* (2013.01); *G07D 7/12* (2013.01); *G07D 7/185* (2013.01); *G07D 7/187* (2013.01); *G07D 7/20* (2013.01); *G07D 7/2008* (2013.01); *G07D 7/2016* (2013.01); *G07D 11/0033* (2013.01); *G07D 11/0051* (2013.01); *G07D 11/0078* (2013.01); *G07D 11/0084* (2013.01); *G07D 11/0087* (2013.01); *G07F 7/00* (2013.01); *G07F 7/04* (2013.01); *G07F 19/206* (2013.01); *G01N 2291/0237* (2013.01); *G01N 2291/048* (2013.01); *G07D 2207/00* (2013.01)

(58) Field of Classification Search
USPC .................. 194/206, 207; 209/534; 235/379
See application file for complete search history.

(56) References Cited

U.S. PATENT DOCUMENTS

| | | |
|---|---|---|
| 8,510,062 B2 | 8/2013 | Domke et al. |
| 8,837,804 B2 | 9/2014 | Su et al. |
| 8,917,386 B2 | 12/2014 | Holl et al. |
| 2006/0287842 A1 | 12/2006 | Kim |
| 2007/0100623 A1 | 5/2007 | Hentschel et al. |
| 2009/0252381 A1 | 10/2009 | Nishikawa |
| 2009/0312957 A1 | 12/2009 | Domke et al. |
| 2010/0128934 A1 | 5/2010 | Su et al. |
| 2013/0088712 A1 | 4/2013 | Holl et al. |
| 2014/0290367 A1 | 10/2014 | Domke et al. |

FOREIGN PATENT DOCUMENTS

| | | |
|---|---|---|
| DE | 102010021803 A1 | 12/2011 |
| DE | 102011117239 A1 | 5/2013 |
| WO | 2008128755 A1 | 10/2008 |
| WO | 2011147575 A1 | 12/2011 |

OTHER PUBLICATIONS

International Search Report from corresponding PCT Application No. PCT/EP2014/002466, Dec. 10, 2014.
International Preliminary Report on Patentability from corresponding PCT Application No. PCT/EP2014/002466, Mar. 15, 2016.

METHOD FOR CHECKING A VALUE DOCUMENT

BACKGROUND

The present invention relates to a method for checking a value document and a corresponding checking device.

Value documents are understood to be sheet-shaped objects that represent for example a monetary value or an authorization and hence should not be producible arbitrarily by unauthorized persons. Hence, they have features that are not easily produced, in particular copied, whose presence is an indication of authenticity, i.e. production by an authorized body. Important examples of such value documents are chip cards, coupons, vouchers, checks and in particular banknotes. The value documents can differ respectively with regard to their type, for example in the case of banknotes with regard to their denomination or the nominal value and the currency or in the case of checks with regard to a type of check form determined by the issuer of the check.

Torn or torn-apart value documents are frequently "repaired" with the aid of adhesive strips. The value documents provided with adhesive strips are to be recognized and sorted out upon the checking of the value documents. In the methods so far for recognizing adhesive strips, the thickness of the value documents is checked. However, the detection of adhesive strips is impaired by variations of the detected thickness measuring values. When the adhesive strip is very thin in addition and/or the value document itself already has a pronounced thickness profile, the hitherto recognition of adhesive strips is limited.

SUMMARY

Further, also forgeries of value documents occur again and again, which are referred to as composed forgeries, i.e. a forged value document that is composed of several value document parts adjoining each other at a separating line. A detached part of a value document is connected to a substrate portion, for example a detached part of a value document of a different type or a suitably formed piece of paper, foil, etc., with the aid of adhesive strips, in such a fashion that a structure is created which has roughly the dimensions of the value document. By the recognition of adhesive strips indirectly also such composed forgeries can be recognized. Many composed forgeries, also such without adhesive strip, can be recognized by means of spatially resolved optical measuring methods, as described in WO2011/147575 A1 or WO2008/128755 A1.

It is consequently the object of the present invention to make available an improved method for checking a value document for the presence of a composed forgery.

The object is achieved by a method for checking a value document according to the independent claims. Advantageous embodiments result from the dependent claims and the description.

In a multiplicity of different measuring points on the value document, measuring values of the value document are detected in spatially resolved fashion, which are distributed over the value document two-dimensionally. A two-dimensional network of nodes is formed, wherein every node corresponds to respectively at least one measuring point on the value document. The measuring value detected in the respective measuring point is allocated to the node corresponding to this measuring point. The node network can be formed of measuring points distributed over the entire value document. However, it is also possible to utilize only the measuring points of a section of the value document for forming the node network. It is possible to utilize exactly one measuring point per node, but also several (e.g. mutually adjacent) measuring points can be summed up to form a node.

A network is formed from the two-dimensional node network of the nodes and two additional nodes arranged on two mutually opposing sides of the two-dimensional node network. One of the additional nodes represents a source node forming a source for a (virtual) flow through the network, and the other represents a sink node forming a sink for the (virtual) flow through the network. The (virtual) flow is merely a mathematical auxiliary quantity which does not describe a physical flow (for example the flow of a physical medium).

For each pair of two adjacent nodes of the network respectively one capacity value is determined which is a measure for the maximally possible flow between the two adjacent nodes. The capacity value of the respective pair of nodes results from mutually comparing the measuring values of the two adjacent nodes, ascertaining respectively one capacity value on the basis of this comparison and allocating the respective capacity value to a connecting line between the two adjacent nodes of the respective pair of adjacent nodes the measuring values of which were mutually compared. On the basis of the ascertained capacity values, the maximally possible flow from the source node through the network to the sink node is then computed with the aid of a numerical optimization method. And in dependence on the computed maximally possible flow through the network, the value document is classified as suspected or not suspected of forgery, in particular in view of the presence of a composed forgery.

The maximally possible flow through the network is a measure for the degree of probability of the value document having a continuous object along a direction transverse (i.e. oblique or perpendicular) to the direction of the network, said object indicating a manipulation of the value document, such as e.g. an adhesive strip or a separating line of a composed forgery. Continuous means that the object extends from one value document edge to the opposite value document edge (or at least has an extension that corresponds almost to the size of the node network in this direction). The object can be of straight or also curved configuration. A small maximally possible flow suggests a high probability of the presence of a continuous or elongate object, a great maximally possible flow correspondingly suggests a low probability of the presence of a continuous or elongate object (e.g. adhesive strip and/or separating line). Since the maximally possible flow is particularly sensitive to such continuous objects and most composed forgeries have a continuous object (separating line and/or adhesive strip), the method according to the invention is very suitable for recognizing composed forgeries.

The classification can be effected by comparing the maximally possible flow through the network to a flow threshold and classifying the value document as suspected of forgery if the maximally possible flow undershoots or reaches the flow threshold and as not suspected of forgery if the maximally possible flow overshoots the flow threshold. However, the maximally possible flow can also be evaluated together with further indicators of the presence of a composed forgery, in order to derive therefrom a resulting forgery probability for the value document in question.

In the method according to the invention, no binary decision is taken for each individual measuring point whether this measuring point is suspected of forgery or not, but a more integral approach is taken, which takes account of the entire or at least a large part of the value document. This is achieved by the determination of the respective capacities for the flow and the computation of the maximally possible flow. The latter indicates the degree of certainty with which the decision is taken whether the value document is suspected of forgery or not. By choosing the flow threshold it is therefore possible to choose as desired by the user of the method whether the check is to be effected more strictly or less strictly.

In the computation of the maximally possible flow through the network it is assumed e.g. that a respective connecting line exists between the source node and the nodes of the network adjacent thereto, said connecting line having a nominal capacity C, and that there is a respective connecting line between the sink node and the nodes of the network adjacent thereto, said connecting line having the nominal capacity C.

For computing the maximally possible flow a numerical optimization method is utilized, wherein the flow through the network is maximized under the following conditions:

a) that the flow through each connecting line between two nodes is at most as great as the capacity $c_{ij}$ between these two nodes, and
b) that for each of the nodes, except for the source node and the sink node, it is valid that the flow flowing into the respective node is as great as the flow flowing out of the respective node (flow maintenance), and
c) that the flow flowing into the sink node is as great as the flow flowing out of the source node.

For each of the measuring points on the banknote a node is defined, to which the measuring value detected in the respective measuring point is allocated. The node receives either the detected measuring value itself or the measuring value minus an offset or a value derived therefrom. As offset e.g. the average measuring value of the value document in question can be deduced or a distribution of the measuring value expected within the framework of a parametric model for the respective value document type in the respective position of the value document. The parametric model is based on learning data ascertained for the respective value document type, can be obtained by means of principal axis transformation and delivers the best possible approximation of the respective distribution of the measuring values on the respective value document. To the respective node there is then allocated the measuring value detected at the respective measuring point minus the measuring value expected for the respective measuring point within the framework of the parametric model. This has the advantage that expected measuring value variations within the value document in question (e.g. due to the printed image or due to authenticity features such as e.g. the watermark or security thread) are segregated and do consequently not influence the computation of the maximally possible flow.

In the numerical optimization method utilized for the computation of the maximally possible flow a minimal cut through the network can be ascertained which forms a type of "bottleneck" for the flow through the network. The minimum cut is that section of the value document which acts in limiting fashion on the maximum flow through the network. The position of the minimum cut through the network can then be utilized for determining a position of an object indicating a manipulation (e.g. adhesive strip and/or separating line) on the document. The position of this object ascertained by means of the minimum cut can advantageously be utilized to check the value document for the presence of a composed forgery with the aid of further methods. For the further checking for the presence of a composed forgery it is e.g. assumed that in the region of the ascertained position of the adhesive strip there extends the separating line of the composed forgery. In particular, for this purpose measuring values of the two value document parts divided by the adhesive strip and/or the separating line can be mutually compared. For example, for this purpose thickness measuring values or optical measuring values of the two value document parts are mutually compared in order to check whether the two value document parts have different optical transmission, different fluorescence or different weights per unit area.

The source node and the sink node of the node network are placed at mutually opposing sides of the network. Preferably they are arranged such that the maximally possible flow through the network is computed along a direction which, on the value document, corresponds to that direction that extends perpendicularly to the longitudinal direction of typical adhesive strips/ separating lines of composed forgeries. When the adhesive strip/ the separating line e.g. extends typically parallel to the shorter sides of the (rectangular) value document, the source and the sink node are placed adjacent to the shorter sides of the value document and the maximally possible flow is computed along the longitudinal direction of the value document.

In order to check the value document for the presence of objects (separating line/adhesive strip) of different orientation, the maximally possible flow through the network is computed both for a first direction through the network and in a second direction extending perpendicularly to the first direction. The first direction can e.g. correspond to the longitudinal direction of the value document and the second direction to the transverse direction of the value document.

In a preferred method, for the first direction a first maximally possible flow through the network is computed, and for the second direction a second maximally possible flow through the network is computed. Subsequently, the first maximally possible flow through the network is normalized on the basis of the number of nodes which the network has along the first direction (e.g. the first flow is divided by the number of nodes along the first direction). And the second maximally possible flow through the network is normalized on the basis of the number of nodes which the network has along the second direction (e.g. the second flow is divided by the number of nodes along the second direction). The normalized first maximally possible flow and the normalized second maximally possible flow are subsequently mutually compared and, in dependence on the smaller one of these two normalized maximally possible flows, the value document is classified as suspected of forgery or not suspected of forgery. For example the smaller one of the first and the second maximum flow is compared to a flow threshold and the value document is classified as suspected of forgery if the smaller one of the two normalized maximally possible flows does not overshoot the flow threshold, and as not suspected of forgery if it overshoots the flow threshold.

The value document processing apparatus then sorts the value document in question e.g. into the output section of the apparatus where value documents suspected of forgery are deposited. Subsequently, the value document suspected of forgery is examined more exactly by a person or by machine for whether it actually represents a composed forgery.

However, the method of the invention can also be used for checking the fitness of the value documents. Preferably, for this purpose the value documents are checked by the method of the invention and also with the aid of further methods for the presence of adhesive strips, e.g. with the aid of a track-based thickness measurement. The results of the various adhesive strip checks can be combined and be incorporated in a final fitness assessment of the value document in question.

To determine the respective capacity value of the respective two adjacent nodes $K_i$, $K_j$ of the network, the measuring values of these two nodes are compared to a target value S or a target range B of the respective measuring value. The target value S/ the target range B can be equal for both measuring values or can also be chosen individually, e.g. in dependence on the above-mentioned expected measuring value variations within the value document. The capacity value $c_{ij}$ of the connecting line between these two nodes $K_i$, $K_j$ is chosen in dependence on that one of these two measuring values $I_i$, $I_j$, which deviates more strongly from the target value S/ from the target range B than the other one of these two measuring values. The capacity value $c_{ij}$ is e.g. chosen by assuming a stepped function for the capacity value as a function of the measuring value deviating more strongly, said stepped function having its maximum value in a target range surrounding the target value. The function declining in stepped fashion preferably has a non-abrupt step progression, since such a progression is more error-tolerant than an abrupt stepped progression. This stepped function is preferably configured such that, as a function of the measuring value deviating more strongly, it declines in stepped fashion on one or on both sides of the target range B.

To determine the respective capacity value of the two adjacent nodes of the network, a nominal capacity C>0 is utilized as capacity value if the measuring value deviating more strongly lies within the target range B. And if the measuring value deviating more strongly lies outside the target range, a capacity c is utilized as capacity value (e.g. continuously varying as a function of this measuring value), said capacity c being smaller than the nominal capacity C, wherein 0<c<C. The position of the target value S/ of the target range B is chosen e.g. in dependence on an average measuring value of several measuring points of the value document.

For the invention all measuring methods are suitable which deliver an indication of an object of a composed forgery (separating line, adhesive strip) indicating a manipulation of the value document. Since the two value document parts of the composed forgery are generally manufactured of different materials, they usually also have a different thickness, conductivity, capacity, and different optical and possibly magnetic properties. This generally results in a jump of the respective measuring value at the separating line of composed forgeries. When the separating line is additionally fortified by an adhesive strip, generally also the adhesive strip changes the measuring values in these measuring points, e.g. the thickness measuring values or also the optical measuring values.

The measuring values can in particular be measuring values of the electromagnetic radiation, e.g. optical measuring values detected by a spatially resolved optical measurement of the value document, e.g. by a spatially resolved transmission, remission or luminescence measurement of the value document, e.g. in the visible, UV or IR spectral range. However, the measuring values can also be detected by a spatially resolved measurement of the electromagnetic radiation of the value document in the thermal IR or terahertz spectral range, in remission or transmission.

However, the measuring values can also be ultrasound measuring values detected by a spatially resolved ultrasound transmission or ultrasound remission measurement of the value document, or thickness measuring values of the value document detected by a spatially resolved mechanical thickness measurement or a spatially resolved ultrasound transmission or remission measurement of the value document, in particular by means of a pulse-echo or sonar method, or capacity measuring values detected by a spatially resolved capacity measurement of the value document, or conductivity measuring values detected by a spatially resolved conductivity measurement of the value document, or magnetic measuring values detected by a spatially resolved magnetic measurement of the value document.

However, the measuring values can also be combined measuring values in which respectively two or more different measuring values of the value document are incorporated which were detected on the value document in spatially resolved fashion by different measuring methods. For example the combined measuring value of the respective measuring point can be combined from at least one measuring value of the electromagnetic radiation and at least one ultrasound measuring value allocated to the respective measuring point on the value document. For the purpose of combination, the measuring values themselves detected in the respective measuring point or values derived from the measuring values can be combined arithmetically and, resulting therefrom as described above the respective capacity value can be allocated. Alternatively, for every measuring method initially a measuring-method specific "capacity map" (network) can be formed, which are subsequently joined to form a common map by utilizing either the respectively lower capacity or a combined capacity for the mutually corresponding edges.

In an exemplary embodiment ultrasound measuring values are utilized as measuring values. For determining the respective capacity value of the respectively two adjacent nodes of the network, the ultrasound measuring values of these two nodes are mutually compared and the capacity value is chosen in dependence on the smaller or the greater of these two ultrasound measuring values. As ultrasound measuring value the phase offset of the ultrasound can be utilized which occurs upon transmission through the value document or the ultrasound intensity transmitted by the value document. If the ultrasound measuring value is the ultrasound intensity, the capacity value is chosen in dependence on the smaller one of these two ultrasound intensities. If the ultrasound measuring value is the ultrasound phase offset, the capacity value is chosen in dependence on the greater one of these two ultrasound phase offsets. The capacity value is e.g. chosen in dependence on the smaller one of these two ultrasound intensities by assuming a function rising in stepped fashion for the capacity value as a function of the smaller one of the two ultrasound intensities.

For example, for determining the respective capacity value of the two adjacent nodes of the network, the ultrasound intensities of these two nodes are mutually compared and the smaller one of these two ultrasound intensities is compared to an intensity threshold I'. If the smaller one of the two ultrasound intensities overshoots the intensity threshold I', a nominal capacity C>0 is utilized as capacity value, and if the smaller one of the two ultrasound intensities does not overshoot the intensity threshold I', a smaller nominal capacity c, with 0>c>C, is utilized as capacity value. The intensity threshold to which the smaller one of the two ultrasound intensities is compared is preferably chosen in dependence on the ultrasound intensity transmitted on average through the value document. In particular, the ultrasound intensity transmitted on average through the value document can be utilized as intensity threshold. However, also a predetermined intensity threshold can be utilized alternatively.

Moreover, preferably for a measuring point that has a very great transmitted ultrasound intensity, e.g. an ultrasound intensity that overshoots a predetermined tear threshold $I_R$, it is assumed that this measuring point lies in the region of a tear of the value document. For the tear threshold therein $I_R \gg I'$ is valid. For the node allocated to this measuring point then the detected, very great ultrasound intensity is replaced by a small ultrasound intensity, which is lower than the intensity threshold $I'$. Thereby, with the aid of the method of the invention it is possible to also recognize a composed forgery which has an adhesive strip that covers a tear only partially, wherein the tear continues beyond the adhesive strip, however.

If the phase offset of the ultrasound is utilized as the ultrasound measuring value, for this purpose in the respective measuring point of the value document there is preferably determined the phase difference relative to a reference phase which is detected at such times at which no value document is disposed between the ultrasound transmitters and the ultrasound receivers of the ultrasonic sensor, e.g. in the gap between two value documents transported through the capture area of the ultrasonic sensor. Conversely to the intensity, the adhesive strip leads to a greater phase offset than in the value document regions without adhesive strip. The respective capacity value of two adjacent nodes then receives the great nominal capacity C when the larger one of the two phase offsets of the two nodes does not overshoot a phase offset threshold, and the smaller nominal capacity c, with $0 < c \ll C$, when the larger one of the two phase offsets overshoots the phase offset threshold. Alternatively, also a function declining in stepped fashion can be utilized for the phase offset as a function of the larger one of the two phase offsets. In the case of a measuring point of the value document having a very small or almost negligibly small phase offset it is assumed that the value document has a tear there. For the node allocated to this measuring point then the detected, very small ultrasound phase offset is replaced by a great ultrasound phase offset. In this fashion, with the aid of the method of the invention also a composed forgery can be recognized which has an adhesive strip that covers a tear only partially, wherein the tear continues beyond the adhesive strip, however.

The invention also relates to a checking device for checking value documents that is configured to perform the method of the invention. The checking device comprises a sensor configured for the spatially resolved detection of measuring values in a multiplicity of different measuring points on the value document. For example the sensor has several measuring tracks transversal to a transport direction of the value document, along which the value document to be checked is transported past the sensor. The sensor has measuring devices corresponding to its utilized measuring method (cf. the above-mentioned measuring methods). The checking device further comprises an evaluation device configured to classify the value document as suspected of forgery or not suspected of forgery in dependence on the computed maximally possible flow through the network.

The detected measuring values can be evaluated in dependence on the value document type of the value document. In dependence on the value document type, e.g. certain sections of the value document can be exempt upon the checking of the value document, i.e. not be taken into account, e.g. such sections where the value document has a foil element. If the detected intensities are compared to an intensity threshold, the intensity threshold $I'$ can be chosen in dependence on the value document type, wherein for thick value documents a higher intensity threshold $I'$ is chosen than for thin value documents.

For performing the check, the evaluation device can contain in particular a processor, for example a microcontroller or a digital signal processor and/or an FPGA and a memory. In the memory in particular instructions of a computer program can be stored, upon the execution of which by the processor method steps of the method of the invention are executed after the detection of the measuring values. The evaluation device can be accommodated with the sensor in the same housing or spatially separately therefrom.

A further object of the invention is an apparatus for processing value documents, preferably for sorting value documents, having a feeding device for value documents to be processed, an output device for value documents having at least two output sections for accommodating processed value documents, a transport device for transporting individual value documents from the feeding device along a transport path to the output device, a checking device according to the invention for classifying the value document as suspected of forgery or not suspected of forgery, which is arranged such that the transport path extends through a capture area of the sensor, and a control device which, in dependence on the classification of the value document by the checking device, so drives the transport device for a value document transported by the transport device that the value document is transported into a first one of the output sections or into a second one of the output sections.

BRIEF DESCRIPTION OF THE DRAWINGS

The invention will hereinafter be explained by way of example with reference to the following figures. There are shown.

DETAILED DESCRIPTION OF VARIOUS EMBODIMENTS

Figure 1:
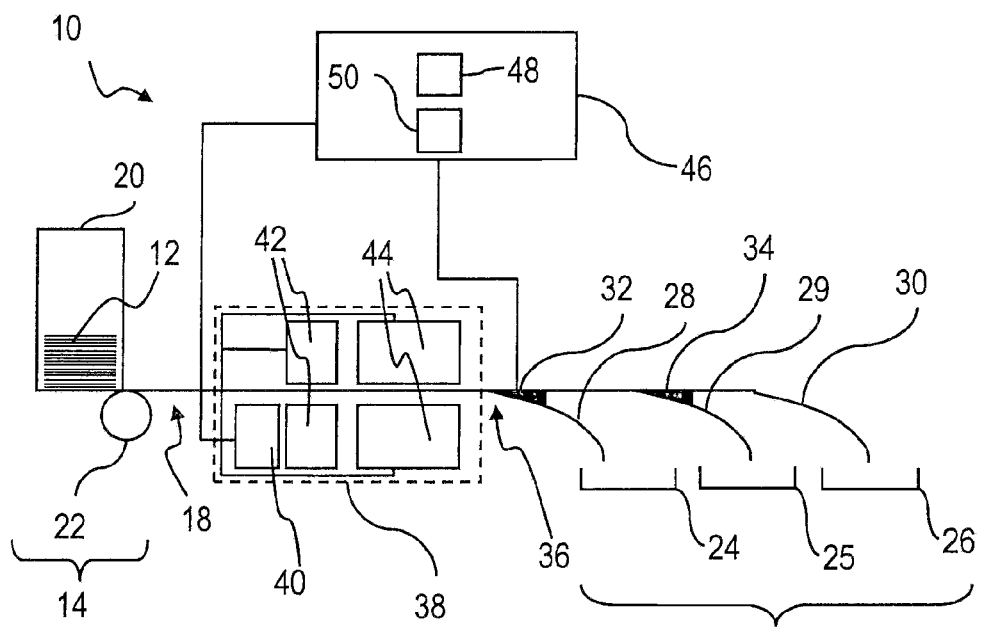
FIG. 1 a schematic representation of a banknote processing apparatus.

In FIG. 1 a value document processing apparatus 10 for sorting value documents is shown, in the example an apparatus for processing banknotes. It has a feeding device 14 for feeding the value documents, an output device 16 for accommodating processed, i.e. sorted, value documents, and a transport device 18 for transporting individual value documents from the feeding device 14 to the output device 16. The feeding device 14 in the example comprises an input pocket 20 for a value document stack and a singler 22 for singling the value documents of the value document stack from the input pocket 20. The output device 16 in this example comprises three output sections 24, 25 and 26, into which processed value documents can be sorted in accordance with the result of the processing in each case. Each of the output sections comprises a stack pocket and a (not shown) stacking wheel, by means of which fed value documents can be deposited in the stack pocket. The transport device 18 has at least two, in the example three branches 28, 29 and 30, at the ends of which respectively one of the output sections 24, 25, 26 is arranged. At the branches gates 32 and 34 controllable by actuating signals are present, by means of which gates value documents can be fed in dependence on actuating signals to the branches 28 to 30 and thus to the output sections 24 to 26.

On a transport path 36 defined by the transport device 18, between the feeding device 14 and the first gate 32 after the singler 22 in the transport direction, a sensor device 38 is arranged which measures, while value documents are transported past, physical properties of the value documents and forms sensor signals reproducing the measuring results. In this example the sensor device 38 has three sensors, namely an optical reflectance sensor 40 capturing a reflectance image of the value document, an optical transmission sensor 42 capturing a transmission image of the value document and a transmission ultrasonic sensor 44 detecting ultrasound measuring values of the respective value document in transmission. The measuring points where the ultrasound measuring values are detected are distributed two-dimensionally over the respectively checked value document.

The ultrasonic sensor can emit the ultrasound continuously or in pulses onto the value document and capture the ultrasound transmitted by the value document. Within the framework of the present invention, ultrasound is understood as sound that has a frequency higher than 20 kHz, preferably higher than 40 kHz. Particularly preferably, the frequency of the ultrasound is below 800 kHz. When ultrasound pulses are utilized, the frequency is understood to be the arithmetic average over the frequencies of the pulse.

A control and evaluation device 46 is connected via signal lines to the sensor device 38 and the transport device 18, in particular the gates 32 and 34. In connection with the sensor device 38, it classifies the respective checked value document into one of predetermined sorting classes in dependence on the sensor signals of the sensor device 38, and by emitting actuating signals drives the gates 32 and/or 34 such that the value document is output in accordance with its sorting class ascertained upon classification to an output section allocated to the class. The allocation to one of the predetermined sorting classes is effected in dependence on at least one predetermined sorting criterion. For example the value documents are sorted according to authenticity and possibly according to value document type and/or state of fitness (fit/unfit).

The control and evaluation device 46 has corresponding interfaces for the sensor device 38 and has a processor 48 and a memory 50 connected to the processor 48, in which there is stored at least one computer program with program code upon the execution of which the processor 48 controls the apparatus and/or evaluates the sensor signals for ascertaining a sorting class of a checked value document, and drives the transport device 18 in accordance with the evaluation. For example the control and evaluation device 46 ascertains from the analog or digital sensor signals of the sensors of the sensor device 38 upon an evaluation of sensor signals at least one value document property that is relevant for the checking of the banknotes with reference to their authenticity and/or state. Preferably, several of these properties are used for evaluation, e.g. optical properties and acoustic properties of the value document. In dependence on the ascertained properties, the control and evaluation device 46 then ascertains an overall result for the check of the respective value document and, in dependence on the result, sends a control signal for the gates 32, 34.

For the processing of value documents 12, value documents 12 inserted into the input pocket 20 are singled by the singler 22 and fed to the transport device 18 which transports the singled value documents 12 past the sensor device 38. This detects the properties of the value documents 12, wherein sensor signals are formed which reproduce the properties of the respective value document. The control and evaluation device 46 captures the sensor signals, in dependence on these ascertains a sorting class of the respective value document, and in dependence of the result controls the gates such that the value documents are transported in accordance with the ascertained sorting class into an output section allocated to the respective sorting class.

Figure 2:
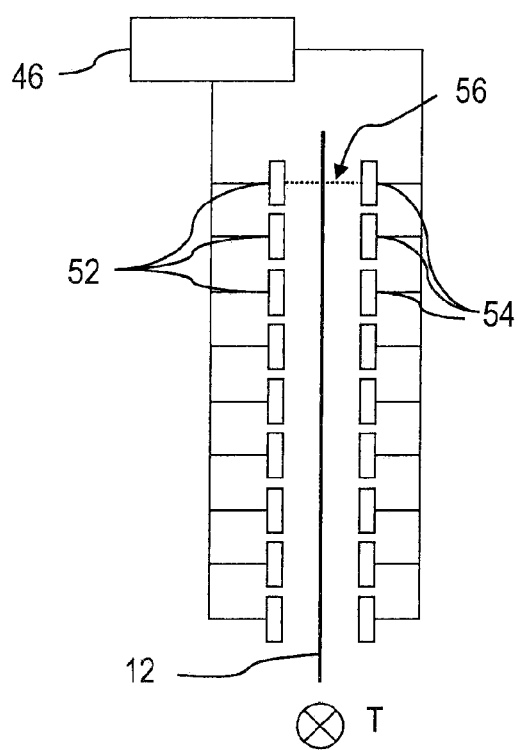
FIG. 2 a schematic representation of an ultrasonic sensor of the banknote processing apparatus in FIG. 1 with a control and evaluation device in a view along a transport direction of banknotes, FIG. 3a-3d a schematic representation of a banknote with an adhesive strip (FIG. 3a), the progression of the transmitted ultrasound intensity along the longitudinal direction of the banknote (FIG. 3b), a network of nodes for the banknote of FIG. 3a (FIG. 3c) and an illustration of the capacity values of the pairs of adjacent nodes (FIG. 3d), FIG. 4 the method steps of the method of the invention, FIG. 5 a non-abrupt stepped function for determining the capacity values as a function of the smaller one of the two intensities of a pair of nodes, FIG. 6 a stepped function declining on both sides of a target range for determining the capacity value of the pairs of nodes.

In the first exemplary embodiment the sorting class is ascertained on the basis of ultrasound properties of the value document. The transmission ultrasonic sensor 44, which in this example has the following structure (cf. FIG. 2), serves for this purpose: The sensor 44 has several ultrasonic converters 52 arranged in a plane parallel to the transport path 36 of the transported value documents 12. By the control and evaluation device 46 the ultrasonic converters 52 are driven to emit ultrasound pulses onto the banknote and thus serve as ultrasound transmitters. Opposite the ultrasonic converters or transmitters 52 with reference to the transport path 36, there is arranged the same number of ultrasonic converters 54 serving as ultrasound receivers, which are connected to the control and evaluation device 46 via interfaces not shown in the figures and signal connections schematically shown. From a value document 12 transported along the transport path 36, the value document being exposed to ultrasound pulses of the ultrasound transmitters 52, the ultrasound receivers 54 detect the ultrasound measuring values of the value document.

To each of the ultrasound transmitters 52 one of the ultrasound receivers 54 is allocated, such that between these an ultrasound path 56 results, along which an ultrasound pulse emitted by the respective ultrasound transmitter 52 runs through the value document to be checked to the ultrasound receiver 54 allocated thereto. With each pair of ultrasound transmitters and ultrasound receivers allocated thereto or with each ultrasound path 56 in connection with the control and evaluation device 46, thereby a value for the ultrasound measuring value of the value document 12 can be ascertained in the location exposed to the ultrasound. To capture the ultrasound measuring values the control and evaluation device 46 captures the sensor signals of the ultrasound receivers 54 at constant time intervals, the sensor signals reproducing the ultrasound measuring values of individual received ultrasound pulses as a function of the time and thus, due to the constant transport speed, also of the location.

The ultrasonic converters 52 and/or 54 are configured such that they are well suited to emit or receive ultrasound pulses of a duration in a range of for example around 30 μs and an ultrasound frequency, i.e. a frequency maximum of the spectrum of the ultrasound pulse, of in the example around 400 kHz. Further, they are dimensioned such that respectively one spot exposed to the ultrasound pulses on the value document 12 transported along the transport path 36 has a diameter of around 2 mm. To each of the spots e.g. the center of the spot is allocated as measuring point. The ultrasound measuring value ascertained in each case is stored such that it is allocated to the measuring point for which it was captured.

In order to suppress an undesired reception of ultrasound pulse echoes, the respective ultrasound receiver for an ultrasound path can be switched on with a delay of somewhat less than the pulse runtime relative to the time of emission of the ultrasound pulse by the ultrasound transmitter for the ultrasound path, and can be switched off again before the double pulse runtime since the time of emission.

In other embodiments the ultrasound paths can also be inclined relative to the plane of the banknote to be examined, in order to avoid the influence of echoes when ultrasound pulses are utilized.

Further, the ultrasound can also be emitted continuously instead of in pulses. In this case, the ultrasound paths are preferably also inclined relative to the banknote to be examined, in order to avoid the occurrence of standing waves.

Figure 3A:
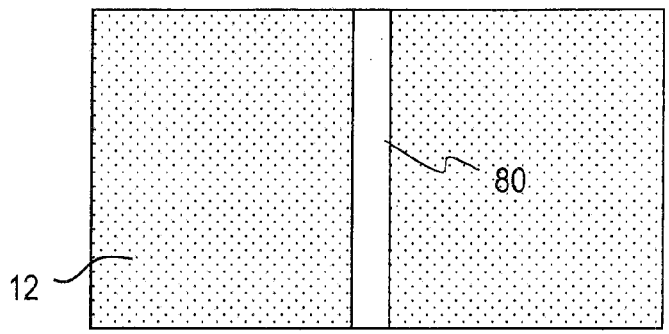

The banknote 12 represented schematically in FIG. 3a has an adhesive strip 80. The adhesive strip 80 can extend over the entire banknote width, but can also cover a shorter section or can be adhesively attached to the banknote in a different orientation, e.g. perpendicularly or obliquely to the shown orientation.

Proceeding from the ultrasound measuring values detected in spatially resolved fashion from the value document, the control and evaluation device 46, more exactly the processor 48, during the processing of program codes of the computer program stored in the memory 50, executes the following method for checking the value document for the presence of a composed forgery. In the following example it is assumed that the respectively detected ultrasound measuring value is the ultrasound intensity transmitted through the value document. Alternatively or additionally to the ultrasound intensity also the ultrasound phase offset can be utilized as ultrasound measuring value, however.

Figure 3B:
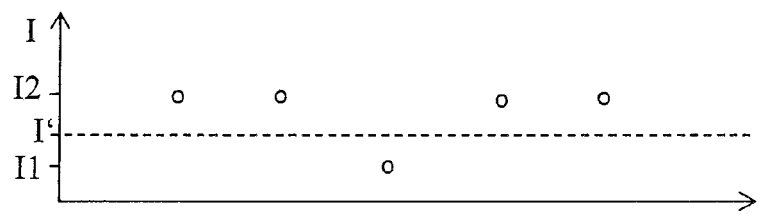
Figure 4:
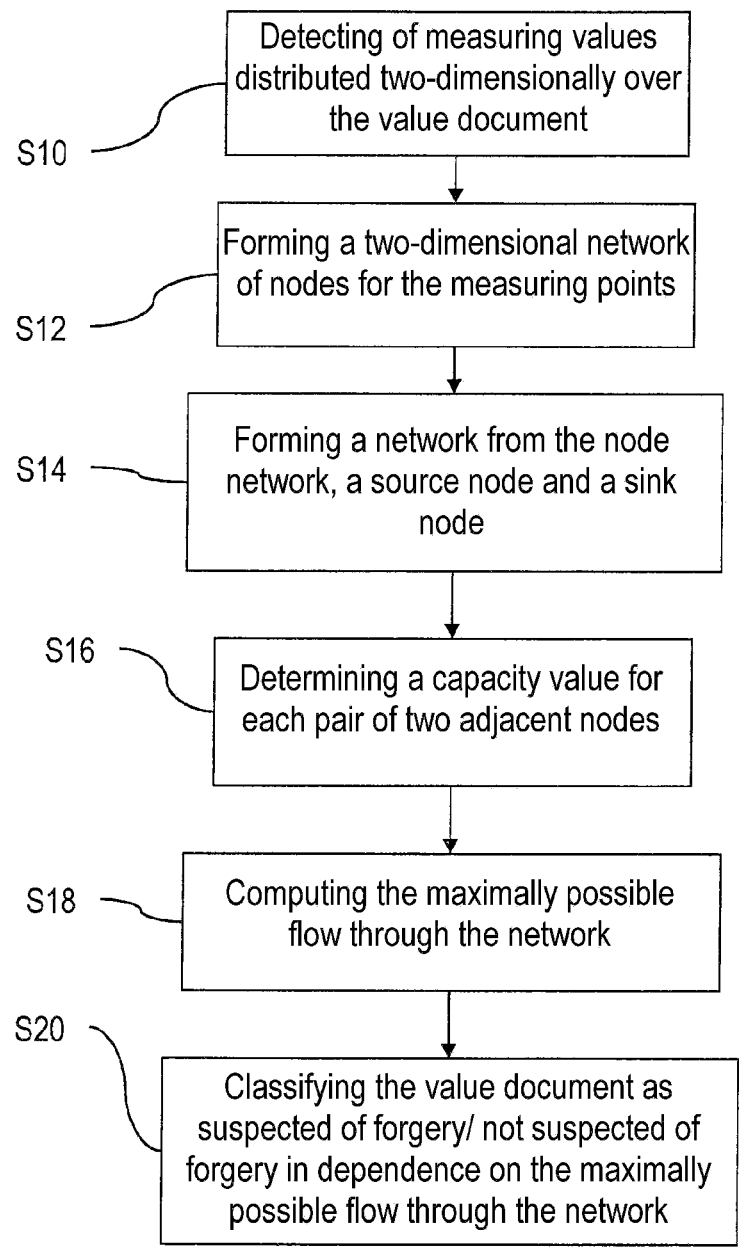

For checking the banknote 12 first the ultrasound measuring values are detected (step S10, cf. FIG. 4). In this example the ultrasound intensity I transmitted through the banknote 12 is used, which is detected by the ultrasonic sensor 44 in the measuring points. The ultrasound intensities detected in the measuring points are intermediately stored in the memory 50 of the control and evaluation device 46. FIG. 3b shows by way of example the detected ultrasound intensity I as a function of the position x in five measuring points along the longitudinal direction of the banknote 12. In the measuring points outside the adhesive strip 80 an ultrasound intensity I2 is detected. In the third measuring point an ultrasound intensity I1 is detected which is reduced in comparison thereto, since the adhesive strip 80 causes an increased ultrasound absorption there.

For each of the measuring points on the banknote a node K is defined to which the ultrasound intensity I is allocated that is detected at the respective measuring point. The node receives either the detected ultrasound intensity itself or the ultrasound intensity minus an offset.

Figure 3C:
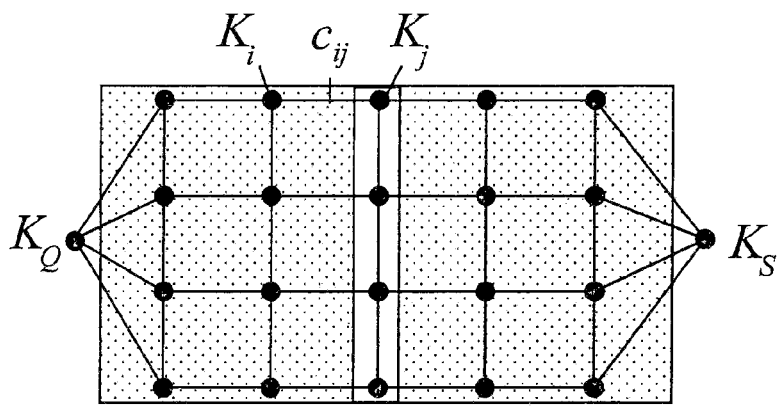

In the example of the FIG. 3c, a network of 20 nodes K is defined, which are distributed regularly over the banknote 12 (step S12). The node $K_j$ and also the further nodes lying in the x position of the adhesive strip 80 have a somewhat smaller ultrasound intensity than the other nodes of the network.

In addition to the nodes of the network, a source node $K_Q$ is defined which lies to the left of the nodes of the left column of the network, and a sink node $K_S$ which lies to the right of the nodes of the right column of the network. The source node $K_Q$ forms a source for a flow through the network and the sink node $K_S$ a sink for this flow. By means of a numerical method the maximally possible flow through the network from the source node $K_Q$ to the sink node $K_S$ is computed (step S14).

Figure 5:
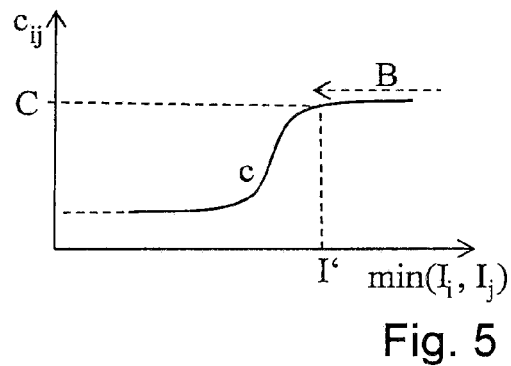

For this purpose a capacity value is determined for each pair of two adjacent nodes of the network, the capacity value being a measure for the maximally possible flow between the two adjacent nodes (step S16). For example the capacity value $c_{ij}$ is determined for the two nodes $K_i$ and $K_j$. To determine the respective capacity value $c_{ij}$ of the two adjacent nodes of the network, the two ultrasound intensities $I_i$ and $I_j$ of these two notes are mutually compared. As intensity $I_i$, $I_j$ the intensity measured in each case minus the above-mentioned offset is utilized. The smaller one of the two ultrasound intensities ($\min(I_i, I_j)$) is compared to an intensity threshold I'. If the smaller one of the two ultrasound intensities ($\min(I_i, I_j)$) overshoots the intensity threshold I' (and thus lies within the target range B), a relatively great nominal capacity C>0 is utilized as capacity value, and if the smaller one of the two ultrasound intensities does not overshoot the intensity threshold I' (and thus lies below the target range B), a smaller nominal capacity c, with 0<c<C, is utilized as capacity value. For a fine incrementation of the capacity values, a continuous curve as a function of the measuring value can be chosen for the capacity c. To determine the capacity values e.g. a function rising in stepped fashion with a non-abrupt stepped curve is utilized, cf. FIG. 5.

To the connecting lines proceeding from the source node $K_Q$ and the connecting lines approaching the sink node $K_S$, the larger capacity C is allocated in any case (independently of the ultrasound intensity of the adjacent node of the network).

For the pair of nodes $K_i$, $K_j$ drawn in FIG. 3c the node $K_j$ delivers the smaller one of the two ultrasound intensities ($\min(I_i, I_j)$)=I1. Taking the intensity threshold I' as a basis which lies between I1 and I2, a capacity value $c_{ij}$=c<C results for the pair of nodes $K_i$, $K_j$. For the node pairs where both nodes have an intensity above the intensity threshold I' ($\min(I_i, I_j) \geq I'$), there consequently results respectively the greater capacity value C. The capacity values resulting for the banknote 12 from FIG. 3a are sketched in FIG. 3d, wherein the thickness of the respective connecting line between two adjacent nodes represents the respective capacity value. Those connecting lines which proceed from or approach any one of the nodes of the third column thus receive the smaller capacity c (thin connecting line), the other connecting lines the greater capacity C (thicker connecting line).

Subsequently, the maximally possible flow through the network is computed, i.e. the greatest possible flow which can flow from the source node $K_Q$ through the network of nodes to the sink node $K_S$ (step S18). This is performed preferably by means of a numerical optimization method. For example Hassin's algorithm is utilized for this purpose, cf. R. Hassin, Maximum flows in (s, t) planar networks, Information Processing Letters, vol. 13, no. 3, pp. 107, 1981. However, also other computation methods can be utilized by which a maximization of the flow can be obtained. The computed capacity values therein determine the maximally possible flow that is possible between two of the nodes in each case. The actual flow resulting between two nodes after maximization of the flow can at most be as great as the capacity of the connecting line between these two nodes. The numerical optimization method is based on the following conditions a) that the flow through any connecting line between two nodes is at most as great as the capacity $c_{ij}$ between these two nodes b) that for each of the nodes, with the exception of the source node and the sink node, it is valid that the flow flowing into the respective node is as great as the flow flowing out of the respective node (flow maintenance)

c) that the flow flowing into the sink node is as great as the flow flowing out of the source node.

Figure 3D:
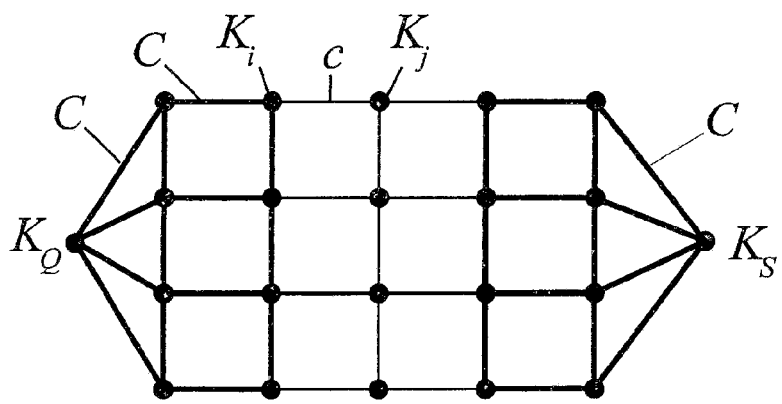

It can be gathered from FIG. 3d already that the flow that is possible from the source node $K_Q$ through the network to the sink node $K_S$ is limited by the low capacity values of the nodes in the region of the adhesive strip 80. These nodes form a "bottleneck" for the flow through the network.

In a second exemplary embodiment the light intensity transmitted through the value document in the respective measuring point is utilized as measuring value, the light intensity being detected under dark-field illumination. As is known, with a dark-field transmission measurement the separating lines at which composed forgeries are joined can be found, cf. in this regard WO-2011147575-A1. It has been found that, when the two value document parts are slightly spaced apart from each other at the separating line, usually an increased dark-field transmission intensity results at this separating line. An increased transmission intensity is detected here regardless of whether the continuous separating line is completely or partially covered by an adhesive strip or not. When the two value document parts overlap slightly, there results a reduced dark-field transmission intensity in contrast.

Figure 6:
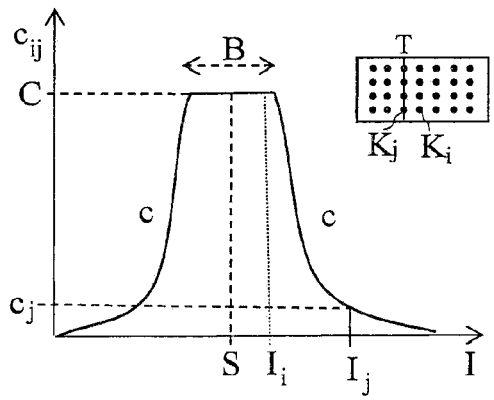

For the transmission intensity to be normally expected from the value document, according to the second exemplary embodiment a target value S and a target range B surrounding the former is assumed, which can be valid locally for the respective region of the value document or also for the complete value document, cf. FIG. 6. The position of the target value S and the width of the target range B are based on the transmission intensities usually detected in the respective value document. The two intensities $I_i$, $I_j$ drawn into FIG. 6 are the dark-field transmission intensities of two adjacent nodes $K_i$, $K_j$ at a separating line T of a composed forgery (cf. FIG. 6 top right), where the value document parts are mutually spaced apart. In FIG. 6, top right, a network of nodes (black dots) is drawn in by way of example, which nodes are distributed across the composed forgery. The measuring value $I_j$ was detected at a node $K_j$ lying directly on the separating line T, the measuring value $I_i$ at a node $K_i$ lying to the right of the separating line T. On the separating line T of the two value documents parts, consequently a substantially greater transmission intensity $I_j$ is detected (in comparison to the intensity $I_i$ and in comparison to the target range B). In the example of FIG. 6 thus the measuring value $I_j$ is that one of the two measuring values $I_i$, $I_j$ which deviates more strongly from the target value S. Correspondingly, to the connecting line between the node pair $K_i$, $K_j$, the capacity value $c_j$ is allocated, as results for $I_j$ from the progression of the curve in FIG. 6. In this case the node $K_j$ on the separating line leads to a reduced capacity $c_j<C$, which limits the flow through the network.

Otherwise, if the two value document parts of the composed forgery overlap slightly at the separating line T, the measuring value detected directly on this separating line would show a smaller dark-field transmission intensity in comparison to the target range B, i.e. would be to the left of the target range B in FIG. 6. Also in this case this measuring value would deviate more strongly from the target value S than a measuring value ($I_i$) detected next thereto. Also in this case the intensity value $I_j$ detected on the separating line determines the capacity of the connecting line between the nodes i and j. Also in this case the node j on the separating line T leads to a reduced capacity $c_j<C$, which limits the flow through the network.

After the capacity values of all node pairs were determined, the flow through the network maximally possible at these capacities is ascertained under the above-mentioned framework conditions. The computed maximally possible flow is then utilized for classifying the value document. If there results a great maximally possible flow, e.g. a flow that reaches or overshoots a predetermined flow threshold, it is concluded therefrom that the value document has no adhesive strip and/or no separating line. In contrast, if the maximally possible flow is below the predetermined flow threshold, the respective value document is classified as suspected of forgery and sorted out.

The invention claimed is:

1. A method for checking a value document, with the following steps of:

detecting in spatially resolved fashion measuring values (Ii, Ij) in a plurality of different measuring points on the value document which are distributed over the value document two-dimensionally;

forming a two-dimensional network of nodes (Ki, Kj), wherein each node corresponds to at least one measuring point on the value document, and allocating the measuring value detected in the respective measuring point to the node corresponding to this measuring point;

creating two additional nodes arranged on mutually opposing sides of the two-dimensional network, and connecting the two additional nodes with the two-dimensional network of nodes (Ki, Kj), wherein one of the additional nodes is a source node (KQ) forming a source for a flow through the network, and the other one is a sink node (KS) forming a sink for a flow through the network;

determining respectively one capacity value for each pair of two adjacent nodes (Ki, Kj) of the network, said capacity value being a measure of the maximally possible flow between the two adjacent nodes, by mutually comparing the measuring values (Ii, Ij) of respectively two adjacent nodes (Ki, Kj) of the network, ascertaining respectively one capacity value (cij) for each of the pairs of adjacent nodes on the basis of this comparison and allocating the respective capacity value (cij) to a connecting line between the two adjacent nodes (Ki, Kj) of the respective pair of adjacent nodes whose measuring values have been mutually compared;

computing the maximally possible flow from the source node (KQ) through the network to the sink node (KS) on the basis of the ascertained capacity values (cij);

classifying the value document, in particular in view of the presence of a composed forgery, as suspected of forgery or not suspected of forgery in dependence on the computed maximally possible flow through the network.

2. The method according to claim 1, wherein, for checking the value document, the maximally possible flow through the network is compared to a flow threshold and the value document is classified as suspected of forgery in view of the presence of a composed forgery, if the maximally possible flow undershoots or reaches the flow threshold, and as not suspected of forgery in view of the presence of a composed forgery, if the maximally possible flow overshoots the flow threshold.

3. The method according to claim 1, wherein for computing the maximally possible flow a numerical optimization method is utilized in which a minimum cut through the network is ascertained that forms a "bottleneck" for the flow through the network, and that in the case that the value document is classified as suspected of forgery, the position of the minimum cut through the network is utilized for determining the position of an adhesive strip (80)/ a separating line (T) of the value document, wherein the position of the adhesive strip (80)/ the separating line (T) ascertained by means of the minimum cut is utilized in particular to check the value document for the presence of a composed forgery with the aid of further methods.

4. The method according to claim 1, wherein to the respective node there is allocated the measuring value detected in the respective measuring point minus a measuring value to be expected for the respective measuring point within the framework of a parametric model.

5. The method according to claim 1, wherein the maximally possible flow through the network is computed along a direction which on the value document corresponds to that direction which extends perpendicularly to the longitudinal direction of typical adhesive strips (80)/ typical separating lines (T), wherein the maximally possible flow is computed along a direction that corresponds to the longitudinal direction of the value document.

6. The method according to claim 1, wherein the maximally possible flow through the network is computed both for a first direction through the network and for a second direction extending perpendicularly to the first direction, wherein the first direction corresponds in particular to the longitudinal direction of the value document and the second direction corresponds in particular to the transverse direction of the value document.

7. The method according to claim 6, wherein
the first direction a first maximally possible flow through the network is computed, and for the second direction a second maximally possible flow through the network is computed;
the first maximally possible flow through the network is normalized on the basis of the number of nodes which the network has along the first direction;
the second maximally possible flow through the network is normalized on the basis of the number of nodes which the network has along the second direction;
the normalized first maximally possible flow and the normalized second maximally possible flow are mutually compared and the value document is classified as suspected of forgery or not suspected of forgery in dependence on the smaller one of the two normalized maximally possible flows.

8. The method according to claim 1, wherein for determining the respective capacity value (cij) of the respective two adjacent nodes (Ki, Kj) of the network, the measuring values (Ii, Ij) of these two nodes are compared to a target value (S)/ a target range (B) of the respective measuring value and the capacity value (cij) is chosen in dependence on the one of these two measuring values (Ii, Ij) which deviates more strongly from the target value (S)/ from the target range (B) than the other one of the two measuring values (Ii, Ij).

9. The method according to claim 8, wherein the capacity value (cij) is chosen by assuming for the capacity value (cij) as a function of the measuring value that deviates more strongly from the target value/ from the target range a stepped function which has its maximal value (C) in a target range (B) surrounding the target value (S) and which, as a function of the measuring value deviating more strongly, declines in stepped fashion on one side or on both sides of the target range (B).

10. The method according to claim 9, wherein for determining the respective capacity value (cij) of the two adjacent nodes of the network, if the more strongly deviating measuring value lies within the target range (B), a nominal capacity C>0 is utilized as capacity value (cij), and, if the more strongly deviating measuring value lies outside of the target range (B), a capacity c is utilized as capacity value (cij) which is smaller than the nominal capacity C, wherein 0<c<C.

11. The method according to claim 8, wherein the position of the target value (S)/ of the target range (B) is chosen in dependence on an average measuring value of several measuring values detected on the value document.

12. The method according to claim 1, wherein the measuring values are measuring values of the electromagnetic radiation that are detected by a spatially resolved electromagnetic measuring of the value document, in particular by a spatially resolved transmission, remission or luminescence measuring of the value document, e.g. in the visible, UV or IR spectral range.

13. The method according to claim 1, wherein the measuring values are ultrasound measuring values detected through a spatially resolved ultrasound transmission or ultrasound remission measurement of the value document.

14. The method according to claim 1, wherein the measuring values are combined measuring values, in which respectively at least two different measuring values of the value document are incorporated which were detected in spatially resolved fashion on the value document by different measuring methods, e.g. that the combined measuring value of the respective measuring point is combined of at least one measuring value of the electromagnetic radiation and at least one ultrasound measuring value allocated to the respective measuring point on the value document.

15. A checking device for checking value documents which is configured to perform a method according to claim 1 and in particular comprises:
a sensor configured to detect in spatially resolved fashion measuring values (Ii, Ij) which are detected of the respective value document in a plurality of different measuring points on the value document, and
an evaluation device configured to execute the method steps according to one or several of the preceding claims and to classify the value document as suspected of forgery or not suspected of forgery in dependence on the computed maximally possible flow through the network.

16. An apparatus for processing value documents, with
a feeding device for value documents to be processed;
an output device for value documents, having at least two output sections for accommodating processed value documents;
a transport device for transporting the value documents from the feeding device along a transport path to the output device;

a checking device according to claim 15 that is arranged such that the transport path of the value document extends through a capture area of the sensor of the checking device; and a control device configured to so drive the transport device for each of the value documents transported by the transport device that the respective value document, in dependence on the classification effected by the checking apparatus, is transported into a first output section or into a second one of the output sections of the apparatus.

\* \* \* \* \*